United States Patent [19]

Lehmann et al.

[11] 4,250,141
[45] Feb. 10, 1981

[54] COLUMN FOR THE REMOVAL OF UNDESIRED SUBSTANCES FROM A LIQUID MIXTURE

[75] Inventors: Hans-Dieter Lehmann; Peter Konstantin, both of Hechingen, Fed. Rep. of Germany

[73] Assignee: Gambro Dialysatoren GmbH & Co. KG, Fed. Rep. of Germany

[21] Appl. No.: 969,847

[22] Filed: Dec. 15, 1978

[30] Foreign Application Priority Data

Dec. 16, 1977 [SE] Sweden .................. 7714336

[51] Int. Cl.³ .................. A61M 1/03; B01D 15/04
[52] U.S. Cl. .................. 422/44; 210/289; 210/445; 210/446; 210/483; 210/660; 210/679; 210/927
[58] Field of Search .................. 422/44; 210/36, 24, 210/289, 445, 446, 483, DIG. 23

[56] References Cited

U.S. PATENT DOCUMENTS

| 2,631,921 | 3/1953 | Odell | 210/24 UX |
|---|---|---|---|
| 2,682,268 | 6/1954 | Ryan et al. | 422/44 |
| 3,163,597 | 12/1964 | Thrun | 210/36 X |
| 3,794,584 | 2/1974 | Kunin | 422/44 X |
| 3,941,573 | 3/1976 | Chapel | 210/446 X |
| 4,048,064 | 9/1977 | Clark | 210/24 X |

FOREIGN PATENT DOCUMENTS

| 982060 | 1/1976 | Canada. |
|---|---|---|
| 2053551 | 5/1972 | Fed. Rep. of Germany. |
| 528287 | 11/1972 | Switzerland. |
| 700765 | 12/1953 | United Kingdom. |
| 774325 | 5/1957 | United Kingdom. |
| 801001 | 9/1958 | United Kingdom. |
| 916565 | 1/1963 | United Kingdom. |
| 1019236 | 2/1966 | United Kingdom. |
| 1054617 | 1/1967 | United Kingdom. |
| 1073727 | 6/1967 | United Kingdom. |
| 1076453 | 7/1967 | United Kingdom. |
| 1119250 | 7/1968 | United Kingdom. |
| 1164416 | 9/1969 | United Kingdom. |
| 1215145 | 12/1970 | United Kingdom. |
| 1271007 | 4/1972 | United Kingdom. |
| 1282540 | 7/1972 | United Kingdom. |
| 1357607 | 6/1974 | United Kingdom. |
| 1471162 | 4/1977 | United Kingdom. |
| 1482071 | 8/1977 | United Kingdom. |
| 1492182 | 11/1977 | United Kingdom. |
| 1499347 | 1/1978 | United Kingdom. |
| 1506970 | 4/1978 | United Kingdom. |
| 1507533 | 4/1978 | United Kingdom. |
| 1535443 | 12/1978 | United Kingdom. |

*Primary Examiner*—Barry Richman
*Attorney, Agent, or Firm*—Lerner, David, Littenberg & Samuel

[57] ABSTRACT

A column for removing poisons and/or other undesired substances from a liquid mixture. The column has a mixture of inactive filler particles and active granules positioned therein, with said filler particles being substantially larger than said active granules, (which are selected from adsorbing material and ion-exchanging material). The filler particles are in fixed contact relationship with each other and the active granules completely fill the spaces between the filler particles.

15 Claims, 1 Drawing Figure

U.S. Patent      Feb. 10, 1981      4,250,141
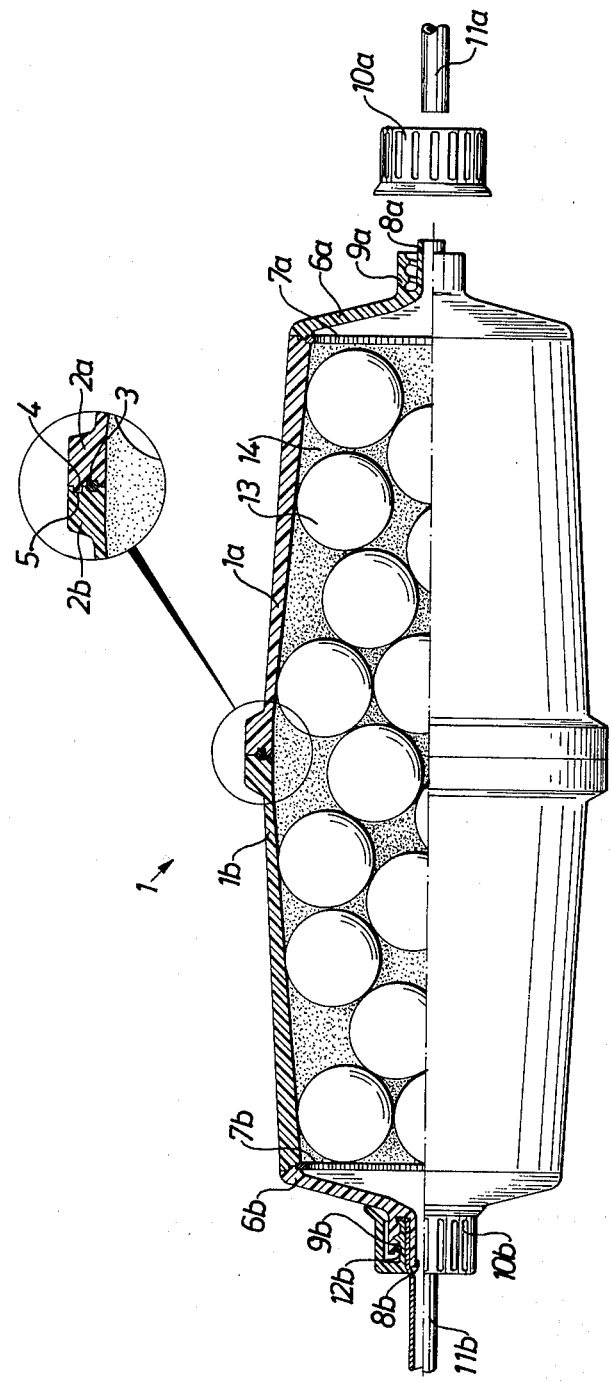

COLUMN FOR THE REMOVAL OF UNDESIRED SUBSTANCES FROM A LIQUID MIXTURE

BACKGROUND OF THE INVENTION

The present invention relates to a column for removing poisons and/or other undesired substances from a liquid mixture. More particularly, the present invention relates to a column for detoxification of blood.

One such column system is disclosed in British Pat. No. 1,482,071. This British Patent discloses a column formed from a biocompatible synthetic polymer material and having inlet and outlet ports for the liquid to be treated. The column is filled with absorptive particulate material, such as activated carbon, located between support means at each end of the column. The construction of the column is said to be such that "non-absorbing dead spaces" between the inlet and outlet ports are minimized.

In a similar vein, U.S. Pat. No. 2,682,268 discloses a column for treating blood comprising a chamber 10 closed at each end by a reticulated screen 12 adapted to hold a granular treatment material 14 in place in the chamber. The chamber 10 is also provided at each end with a suitable end connection 16. The granular treatment material 14, for example, an ion-exchange resin or the like, occupies the volume between the screens 12 to such an extent as to maintain the shape of the body of the column during shipping or handling, but the treatment material does not quite fill the chamber.

Canadian Pat. No. 982,060 discloses a column 10 for removing urea from dialysate solution. The column is filled with at least two layers, one layer being zirconium phosphate 32 and the other being urease in combination with a urease-retaining material 28. The urease-retaining material renders the enzyme urease water-insoluble but allows the urease to retain its ability to enzymatically decompose urea. Magnesium silicate is disclosed as a suitable urease-retaining material. As a liquid containing urea is passed through the urease-retaining layer, the urease converts the urea to ammonium carbonate. The liquid is then passed through the zirconium phosphate layer, which picks up the ammonium ions and replaces them with hydrogen and sodium ions.

Such columns can be used to remove poisons from, for example, blood. However, such columns have certain disadvantages since the same column may not be suitable for use in the treatment of both adults and children. For example, a completely different column capacity is required for detoxification of an adult person than is necessary for a child. Also, it is sometimes necessary to keep the extracorporeal portion of blood considerably smaller with children than with adults.

These column requirements can, of course, be met by using columns of different sizes. However, this requires manufacturing of and maintaining of a stock of such variously sized columns.

Furthermore, when the size of the column is modified, the hydrodynamic conditions in the column are altered. This alteration leads to uncertainty in the results achieved by the treatment and may even substantially complicate the treatment.

SUMMARY OF THE INVENTION

In accordance with the present invention, a column for removing undesired substances from a liquid mixture has been devised including an outer casing having an inlet and an outlet for the liquid mixture. Filler particles, which are substantially inactive to the liquid mixture, partially fill the casing. Active granules fill the remainder of the casing. These active granules are capable of removing the undesired substances from the liquid mixture as the liquid passes through the casing from the inlet to the outlet. The active granules are formed of a material selected from the group consisting of activated absorbing materials and ion-exchanging materials. The filler particles are substantially larger than the active granules. The filler particles also are in contact with each other and extend from the inlet to the outlet with the active granules filling in spaces between the filler particles. Such a column allows for variation in the capacity of the column without changing the size of the column itself. Moreover, by appropriate design of the filler particles, flow through the column can be facilitated and treatment made more effective.

Any of the adsorbing materials and ion-exchanging materials known in the art can be used in the present invention. Preferred adsorbing materials are activated charcoal and absorbing polymer materials, i.e. macroporous polystyrene crosslinked with divinylbenzene, if necessary also carrying functional groups.

The filler particles can be from 5 to 50 times as large as the active granules. Preferably, the filler particles are 10 to 25 times as large as the active granules. Also, the ratio of the volume of the column casing taken up by the filler particles can vary widely depending on the liquid mixture being treated. The filler particles preferably occupy from about 25 to about 75 % by volume of the column casing, and more preferably from about 40 to about 60 % by volume of the column casing.

In a preferred embodiment of the present invention, the filler particles are preferably formed from a biocompatible synthetic polymer material. The casing for the column is also preferably formed of the same biocompatible synthetic polymer material. Any of the known biocompatible synthetic polymer materials can be used for this purpose. Preferred are biocompatible thermoplastic materials as i.e. polyolefins, vinylpolymers, polycarbonates etc.

In another preferred embodiment, the filler particles are given an hydrodynamically resp. hemodynamically favourable shape. A preferable shape for the filler particles is spherical.

In yet another embodiment of the present invention, the column may consist of a substantially cylindrical or doubleconical central casing part between two end parts which are preferably of a conical shape. The end parts also define connecting nozzles which serve as the inlet and outlet for tubing through which the liquid to be treated is supplied and withdrawn, respectively. Supporting layers, preferably in the form of strainers, gauzes or the like, are arranged at the connection between the end parts and the central casing part for supporting or retaining the filler particles and active granules in the central casing part. In a column employing such supporting layers, the filler particles are in contact with each other and extend from one supporting layer to the other. In this manner, the different filler particles can be substantially fixed in relation to one another and in relation to the active granules, thus preventing the risk of particles and granules being set free because of wear. Such a design produces good hydrodynamic conditions which may be improved when used with the combination of active granules and spherical filler particles in accordance with the present invention.

In accordance with a further aspect of the invention, the casing can be manufactured in the form of two substantially identical halves which are joined together in a suitable manner. The halves are preferably welded together.

The column of the present invention is intended primarily for hemoperfusion. In such a use, the active material will preferably consist of activated charcoal. However, it will also be clear to those skilled in the art that the column of the present invention can also be used for other purposes, e.g., for ion-exchance in a manner similar to that described in Canadian Pat. No. 982,060 mentioned above. In such latter use, the active material will, of course, consist of an ion-exchange material.

BRIEF DESCRIPTION OF THE DRAWING

The present invention may be better understood with reference to the FIGURE which is a partial longitudinal cross-sectional view of a column in accordance with the present invention.

DETAILED DESCRIPTION

Referring to the FIGURE, a column in accordance with the present invention is shown in which the column 1 consists of two substantially identical halves 1a and 1b. The two halves are joined together by the use of two flanges 2a and 2b on halves 1a and 1b, respectively. A metal ring 3 is provided to secure the joining of the two halves 1a and 1b. Also, the flange 2a is provided with a bead 4 which fits into a groove 5 in the flange 2b to further secure the halves together.

The ends of the halves 1a and 1b are closed off by means of conical end parts 6a and 6b, respectively. Strainers 7a and 7b are provided at the connection between the respective conical end parts and its associated half. The attachment of the end parts 6a and 6b on the halves 1a and 1b, respectively, can be achieved in any suitable manner, for example, by means of welding.

The end parts 6a and 6b are closed off by connecting nozzles 8a and 8b, respectively. Nozzles 9a and 9b surround the nozzles 8a and 8b, respectively, and are provided with internal threads. The nozzles 9a and 9b fit together with threaded caps 10a and 10b, respectively, and serve to fix tubing 11a to nozzle 8a and tubing 11b to nozzle 8b. As can be seen on the left in the FIGURE, the caps 10a and 10b are provided with internal threads which are adapted to be screwed together with the associated threads of nozzles 9a and 9b so as to provide the above-mentioned fixing. Thread 12b is thus shown for the cap 10b, while the corresponding thread for cap 10a is concealed inside the cap 10a.

The column is filled internally with spherical inactive filler particles 13 which are in contact with each other and extend from strainer 7a to strainer 7b. The spaces between the filler particles 13 are filled by means of a granular activated material 14, e.g., activated charcoal.

It will be clear to those skilled in the art that the capacity of the column illustrated in the FIGURE can be varied within wide limits, while at the same time, allowing advantageous influences on the hydrodynamic conditions.

The following examples are provided to illustrate the column of the present invention, it being understood that such examples are only illustrative and are not deemed to be limiting thereof.

EXAMPLE 1

Five columns prepared in accordance with the present invention were compared with a column available commercially under the trade name ABSORBA ®300C The latter column is normally filled with 700 ml of activated charcoal.

For this comparison, the columns of the present invention were filled with 48 filler spheres having a diameter of 2.4 cm. The column casing and the spheres were formed of polypropylene. The volume of each sphere was thus about 7.24 ml. Accordingly, the 48 spheres provided approximately 347 ml. The size of the spheres was chosen such that the column casings were completely filled between two end supports, i.e., strainers, thereby preventing any displacement of the spheres in relation to one another. The spaces between the spheres in the column casing were filled with activated charcoal.

Both the commercial column and the columns in accordance with the present invention were primed with 130 ml of an isotonic salt solution. Then each column was flushed with two liters of physiological salt solution. The liquid leaving each column was tested to determine the number of particles per ml having sizes greater than or equal to 5 microns and sizes greater than or equal to 2 microns. The results are shown below in Table I along with the acceptable value according to the British Pharmacopaea. In Table I, the columns in accordance with the present invention are labelled columns 1 through 5.

TABLE 1

|  |  | Number of particles per ml | |
|---|---|---|---|
|  |  | $\geq 5\,\mu$ | $\geq 2\,\mu$ |
| Column No. | 1 | 9 | 162 |
|  | 2 | 6 | 125 |
|  | 3 | 5 | 102 |
|  | 4 | 10 | 81 |
|  | 5 | 23 | 92 |
| ADSORBA ® 300C (mean value) |  | 10 | 150 |
| British Pharmacopaea acceptable value (max.) |  | 100 | 1000 |

The results listed in Table 1 demonstrate that the columns of the present invention provide particle numbers similar to the mean value for the commercial product ABSORBA ®300C Also, the particle numbers provided by the columns of the present invention are clearly below the maximum acceptable value according to British Pharmacopaea.

EXAMPLE 2

A column in accordance with the present invention was prepared as described in example 1 above. Blood containing barbital was flushed through this column in accordance with the present invention at a flow rate of 200 ml per minute. Similarly, blood containing barbital also passed at the same flow rate through the commercial column ADSORBA ®300C The starting concentration of the barbital in the blood passed through the column of the present invention was 101.1 mg/1, while the starting concentration of the blood pass through the ADSORBA ®300C column was 99.6 mg/1.

The "clearance" for barbital was determined after the respective blood samples had passed through 15, 30, 60 and 120 foot lengths of the column in accordance with the present invention and the commercial column. "Clearance" is defined by the following formula:

$$\text{"Clearance"} = \frac{C_{in} - C_{out}}{C_{in}} \times Q_B$$

$C_{in}$ = Concentration of poison in the blood which is to be detoxicated.
$C_{out}$ = Concentration of poison in the detoxicated blood at point measured.
$Q_B$ = Blood flow (ml/min).

The total quantity in grams of barbital adsorbing onto the respective columns was also determined.

The results are shown below in Table 2 in which 150 C. designates the column in accordance the present invention.

TABLE 2

|  | Starting concentration (mg/l) | Clearance 15' | 30' | 60' | 120' | Total adsorbing quantity (g) |
|---|---|---|---|---|---|---|
| 150C | 101.1 | 195 | 194 | 192 | 190 | 1.92 |
| ADSORBA ® 300C | 99.6 | 200 | 198 | 194 | 188 | 1.94 |

These results demonstrate that "clearance" for the column of the present invention for barbital is substantially comparable with that for ADSORBA ®300C

EXAMPLE 3

The procedure according to Example 2 was repeated, except phenobarbital was substituted for barbital in a considerably higher starting concentration as indicated in Table 3 below. In Table 3, 150C again indicates the column in accordance with the present invention.

TABLE 3

|  | Starting concentration (mg/l) | Clearance 15' | 30' | 60' | 120' | Total adsorbing quantity (g) |
|---|---|---|---|---|---|---|
| 150C | 310 | 102 | 85 | 77 | 77 | 2.9 |
| ADSORBA ® 300C | 300 | 155 | 147 | 122 | 107 | 4.0 |

The results shown in Table 3 demonstrate that "clearance" for phonobarbital is lower for the column in accordance with the present invention than for the commercial column ADSORBA ®300C. However, since the commerical product contains twice the amount of adsorbents, the "clearance" obtained by the column of the present invention is clearly higher than what might have been expected.

It will be understood that the embodiment described above are merely exemplary and that persons skilled in the art may make many variations and modifications without departing from the spirit and scope of the invention. For example, the shape of a column as well as the contents of the same may be varied within wide limits without exceeding the scope of the invention. All such modifications and variations are intended to be included within the scope of the invention as defined by the appended claims.

What is claimed is:

1. A column for removal of undesired substances from a liquid mixture, comprising an outer casing having an inlet and an outlet for the liquid mixture; filler particles partially filling said casing, which filler particles are substantially inactive to said liquid mixture; and active granules filling the remainder of said casing, said active granules being capable of removing said undesired substances from said liquid mixture as said liquid mixture passes through said casing from said inlet to said outlet and being formed of a material selected from the group consisting of adsorbing material and ion-exchanging material, wherein said filler particles are substantially larger than said active granules and wherein said filler particles are in fixed contact relationship with each other and extend from said inlet to said outlet with said active granules essentially completely filling in spaces between said filler particles.

2. A column according to claim 1, wherein said active granules consist of activated charcoal.

3. A column according to claim 1, wherein said active granules consists of an adsorbing polymer material.

4. A column according to claim 1, wherein said filler particles are about 5 to about 50 times as large as said active granules.

5. A column according to claim 1, wherein said filler particles are about 10 to about 25 times as large as said active granules.

6. A column according to claim 1, wherein said filler particles occupy from about 25 to about 75% by volume of said coulmn casing.

7. A column according to claim 1, wherein said filler particles occupy from about 40 to about 60% by volume of said column casing.

8. A column according to claim 1, wherein said filler particles and said casing are formed of a biocompatible synthetic polymeric material.

9. A column according to claim 1 or 8, wherein said filler particles have hydrodynamically and hemodynamically favourable shapes.

10. A column according to claim 9, wherein said filler particles are spherically shaped.

11. A column according to claim 1, wherein said casing consists of a substantially cylindrical central casing part; two end parts, one on each end of said central casing part, said end parts being conically shaped and defining connecting nozzles which serve as said inlet and said outlet; and supporting means arranged at the connection between said end parts and said central casing part for supporting said filler particles and said active granules in said central casing part.

12. A column according to claim 1, wherein said casing consists of a double-conical central casing part; two end parts, one on each end of said central casing part, said end parts being conically shaped and defining connecting nozzles which serve as said inlet and said outlet; and supporting means arranged at the connection between said end parts and said central casing part for supporting said filler particles and said active granules in said central casing part.

13. A column according to claim 11 or 12, wherein said filler particles completely fill the space in said central casing part between said supporting means.

14. A column according to claim 1 or 12, wherein said casing consists of two substantially identical halves which are joined together.

15. A column according to claim 14, wherein said two halves are welded together.

* * * * *